US010668003B2

(12) United States Patent
Lange et al.

(10) Patent No.: US 10,668,003 B2
(45) Date of Patent: Jun. 2, 2020

(54) PRODUCT AND METHOD FOR THE TEMPORARY SHAPING OF KERATIN-CONTAINING FIBERS

(71) Applicant: Henkel AG & Co. KGaA, Duesseldorf (DE)

(72) Inventors: Julia Bibiane Lange, Bad Bramstedt (DE); Anna Puls, Winsen (DE); Cyrielle Martinez, Hamburg (DE); Bernd Richters, Hamburg (DE)

(73) Assignee: Henkel AG & Co. KGaA, Duesselforf (DE)

( * ) Notice: Subject to any disclaimer, the term of this patent is extended or adjusted under 35 U.S.C. 154(b) by 0 days.

(21) Appl. No.: 15/555,557

(22) PCT Filed: Nov. 11, 2015

(86) PCT No.: PCT/EP2015/076330
§ 371 (c)(1),
(2) Date: Sep. 5, 2017

(87) PCT Pub. No.: WO2016/142013
PCT Pub. Date: Sep. 15, 2016

(65) Prior Publication Data
US 2018/0049967 A1  Feb. 22, 2018

(30) Foreign Application Priority Data
Mar. 9, 2015  (DE) ........................ 10 2015 204 148

(51) Int. Cl.
A61K 8/81      (2006.01)
A61Q 5/06      (2006.01)

(52) U.S. Cl.
CPC .......... A61K 8/8152 (2013.01); A61K 8/8182 (2013.01); A61Q 5/06 (2013.01); A61K 2800/594 (2013.01)

(58) Field of Classification Search
CPC ............ A61K 2800/594; A61K 8/8152; A61K 8/8182; A61Q 5/06
See application file for complete search history.

(56) References Cited

U.S. PATENT DOCUMENTS

| 6,190,647 | B1 | 2/2001 | Karlen et al. |
| 2012/0064023 | A1 | 3/2012 | Knappe et al. |
| 2014/0093467 | A1* | 4/2014 | Knappe ............... A61K 8/8152 424/70.15 |
| 2018/0055756 | A1* | 3/2018 | Lange .................... A61Q 5/06 |
| 2018/0168989 | A1* | 6/2018 | Lange ................. A61K 8/8152 |

FOREIGN PATENT DOCUMENTS

| DE | 102007008089 A1 | 8/2008 | |
| DE | 102011077364 | * 10/2011 | .............. A61K 8/81 |
| DE | 102013225753 A1 | 5/2014 | |
| EP | 1238646 A1 | 9/2002 | |

OTHER PUBLICATIONS

Ashland (Perfectly clear AquaStyle SH-100 polymer for consumer-desirable performance attributes in crystal clear hair gels; http://ashlandstylebook.com/wp-content/uploads/2015/01/ASH-PC7934_AquaStyle_SH_100_Brochure.pdf (Year: 2014).*
EPO, International Search Report and Written Opinion issued in International Application No. PCT/EP2015/076330, dated Jan. 8, 2016.
BASF, "Acrylic Terpolymer Products for Hair-Setting Preparations With a Strong, Long-Lasting Effect (Luvimer)", Sep. 2000.
Jones, Charles, "Multifunctional Synthetic Rheology Modifiers for Personal Care Formulations: More Than Just Thickeners", 2005, Rohm and Haas Company.
Signori, Vittoria, "Acrylates Copolymers—Why do we Need to Neutralize them?", 2006, Cosmetic Science Technology.

* cited by examiner

Primary Examiner — Anna R Falkowitz
(74) Attorney, Agent, or Firm — Lorenz & Kopf, LLP

(57) ABSTRACT

The disclosure relates to a cosmetic composition for the temporary shaping of hair, containing a combination of two specific anionic acrylate copolymers. The cosmetic composition provides an extremely good moisture resistance.

9 Claims, No Drawings

PRODUCT AND METHOD FOR THE TEMPORARY SHAPING OF KERATIN-CONTAINING FIBERS

CROSS-REFERENCE TO RELATED APPLICATION

This application is a U.S. National-Stage entry under 35 U.S.C. § 371 based on International Application No. PCT/EP2015/076330, filed Nov. 11, 2015 which was published under PCT Article 21(2) and which claims priority to German Application No. 10 2015 204 148.4, filed Mar. 9, 2015, which are all hereby incorporated in their entirety by reference.

TECHNICAL FIELD

The present disclosure relates to a cosmetic composition for hair setting and for the temporary reshaping of keratinous fibres, in particular human hair, wherein the composition contains a combination of two anionic acrylate polymers.

BACKGROUND

The temporary styling of hair for a prolonged period of up to several days usually requires the use of active setting agents. Hair treatment means which are used for the temporary shaping of hair therefore play an important part. Corresponding means for temporary reshaping customarily contain synthetic polymers and/or waxes as the active setting agent. Means for assisting the temporary reshaping of keratin-containing fibres may be manufactured in the form of hairspray, hair wax, hair gel, hair mousse, for example.

The most important property of a means for the temporary reshaping of hair, hereinafter also referred to as a styling agent, is that of giving the treated fibres the strongest possible hold in the newly fashioned style—i.e. a style impressed on the hair. This is also referred to as a firm hairstyle hold or the strong hold of the styling agent. The hold of the hairstyle is substantially determined by the nature and quantity of the active setting agents used, wherein, however, the further constituents of the styling agent may also have an influence.

Apart from a high degree of hold, styling agents must meet a whole host of other requirements. These can be roughly divided into properties on the hair, properties of the respective formulation, e.g. properties of the mousse, gel or sprayed aerosol, and properties that relate to the handling of the styling agent, wherein particular importance is attached to the properties on the hair. Particular mention should be made of moisture resistance, low tack and a balanced conditioning effect. Furthermore, a styling agent should be universally applicable to all hair types and be kind to hair and skin.

In order to satisfy the different requirements, a plurality of synthetic polymers has already been developed as active setting agents, which synthetic polymers are used in styling agents. The polymers can be divided into cationic, anionic, non-anionic and amphoteric setting polymers. Ideally, when applied to hair, the polymers produce a polymer film which, on the one hand, gives the hairstyle a strong hold but, on the other hand, is sufficiently flexible not to break when subject to stress. If the polymer film is too fragile, so-called film flakes, in other words residues, are formed which become detached when the hair moves and give the impression that the user of the styling agent concerned has dandruff. Similar problems result when waxes are used in the styling agent as the active setting agent. If the styling agent is a gel or a paste, the polymers should also have thickening properties.

Anionic polymers known in the art which are used in hair-setting products are crosslinked anionic amphiphilic polymers which contain a (meth)acrylic acid unit and a (meth)acrylic acid oxyalkylene alkyl ester unit. Polymers of this kind are described in European patent EP 897 711 B1 and German patent applications DE 102011077364 A1 and DE 102009001978 A1, for example, and are commercially available, e.g. by the name Aculyn®88 (INCI: Acrylates/Steareth-20 Methacrylate Crosspolymer). DE 10 2011 077 364 A1 and DE 10 2009 001 978 A1 relate to the use of a polymer of this kind, in particular also Aculyn® 88, in combination with a further special crosslinked anionic polymer for the temporary reforming of hair.

A structurally similar polymer is commercially available by the name BALANCE® RTF (INCI: Acrylates/Ceteareth-20 Methacrylate Crosspolymer), wherein the function thereof in styling products is substantially that of a thickening agent and film former.

Furthermore, hydrophobically modified acrylate copolymers (INCI: Acrylates Copolymer (and) Water) are commercially available which essentially act as a thickening agent. The AquaStyle® SH-100 Polymer (Ashland Inc.) data sheet describes an acrylate copolymer of this kind and the use thereof in combination with carbomers. Suitability for crystal-clear hair gels, good initial stiffness, moisture resistance and high-humidity curl retention are described.

BRIEF SUMMARY

A cosmetic agent is provided herein for the temporary reshaping of keratinous fibres. The cosmetic composition includes (a) at least one crosslinked acrylate copolymer which is constructed at least from the following structural units (a1) and (a2):

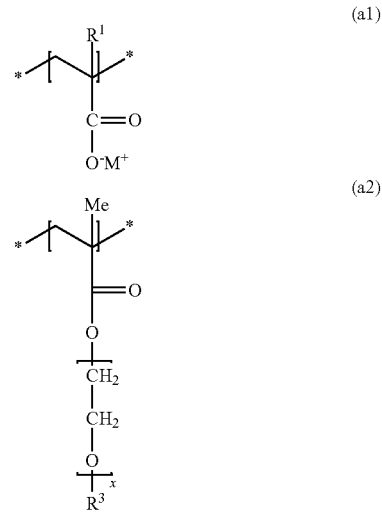

where
$R^1$ stands for a hydrogen atom or a methyl group,
$R^3$ stands for a ($C_8$-$C_{30}$) alkyl group,
$M^+$ stands for a physiologically compatible cation, and
x stands for a whole number from 5 to 35.

The cosmetic composition further includes (b) at least one anionic acrylate copolymer (b). The at least one anionic acrylate copolymer (b) is constructed from at least the following monomer units: (b1) at least one (meth)acrylic acid unit, (b2) at least one (meth)acrylic acid ethyl ester unit, and (b3) at least one (meth)acrylic acid ester unit which is different from the (meth)acrylic acid ethyl ester unit (b2) and exhibits a hydrophobic group as the ester group.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

One problem addressed by the disclosure is that of providing further suitable polymer combinations which are exemplified by good film-forming and/or setting properties, have a very high degree of hold without thereby compromising flexibility and good moisture resistance—in particular sweat and water resistance—and, in addition, are suitable for the production of stable viscous and stable transparent cosmetic compositions. In particular, currently available styling agents can still be improved in that a good combination of stiffness and high-humidity curl retention is not always adequately guaranteed. A problem addressed by the present disclosure is therefore that of providing styling agents which, in addition to the aforementioned properties, particularly produce both good stiffness and also good high-humidity curl retention.

As contemplated herein, this was achieved through a combination of two particular anionic acrylate polymers that differ from one another.

The present disclosure provides:

1. A cosmetic composition for the temporary reshaping of keratinous fibres which contains:

(a) at least one crosslinked acrylate copolymer which is constructed at least from the following structural units (a1) and (a2):

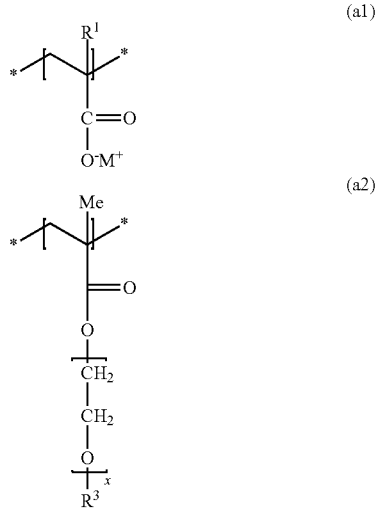

where $R^1$ stands for a hydrogen atom or a methyl group, $R^3$ stands for a $(C_8-C_{30})$ alkyl group, $M^+$ stands for a physiologically compatible cation and x stands for a whole number from 5 to 35 and (b) at least one anionic acrylate copolymer (b) which is constructed from at least the following monomer units:

(b1) at least one (meth)acrylic acid unit (b2) at least one (meth)acrylic acid ethyl ester unit (b3) at least one (meth)acrylic acid ester unit which is different from the (meth)acrylic acid ethyl ester unit (b2) and exhibits a hydrophobic group as the ester group.

2. The cosmetic composition according to point 1, wherein the x in the structural unit (a2) of the crosslinked acrylate polymer (a) stands for a whole number from 10 to 24, further preferably from 16 to 22, most preferably 20.

3. The cosmetic composition according to one of the preceding points, wherein $R^3$ in the structural unit (a2) of the crosslinked acrylate copolymer (a) stands for a $(C_{12}-C_{20})$ alkyl group, further preferably a $(C_{14}-C_{20})$ alkyl group and, in particular, a $(C_{16}-C_{18})$ alkyl group.

4. The cosmetic composition according to one of the preceding points, wherein the composition contains the crosslinked acrylate polymer (a) in a proportion of from about 0.1 to about 5.0% by wt, preferably from about 1.0 to about 4.0% by wt and, in particular, of from about 1.5 to about 3.0% by wt, relative to the total weight of the cosmetic composition.

5. The cosmetic composition according to one of the preceding points, wherein the anionic acrylate polymer (b) exhibits methacrylic acid as the monomer unit (b1) and ethyl acrylate as the monomer unit (b2).

6. The cosmetic composition according to one of the preceding points, wherein the anionic acrylate copolymer (b) has a (meth)acrylic acid alkyl ester as the monomer unit (b3).

7. The cosmetic composition according to one of the preceding points, wherein the composition contains the anionic acrylate copolymer (b) in a proportion of from about 0.1 to about 5.0% by wt, preferably from about 1.0 to about 4.0% by wt and, in particular, from about 1.5 to about 3.0% by wt, relative to the total weight of the cosmetic composition.

8. The cosmetic composition according to one of the preceding points, wherein the anionic acrylate copolymer (b) exhibits a viscosity of from about 60000 to about 120000 cPs where there is a solid content of about 2% by wt in an aqueous neutralised solution at 25° C.

9. The cosmetic composition according to one of the preceding points, wherein the anionic acrylate copolymer (a) is one with the INCI name Acrylates/Ceteareth-20 Methacrylate Crosspolymer, in particular BALANCE® RCF (AkzoNobel).

10. The cosmetic composition according to one of the preceding points, wherein the anionic acrylate copolymer (b) is one with the INCI name Acrylates Copolymer (and) Water, in particular AquaStyle SH-100 (Ashland Inc.).

11. The cosmetic composition according to one of the preceding points, wherein the anionic acrylate copolymer (a) is one with the INCI name Acrylates/Ceteareth-20 Methacrylate Crosspolymer and the anionic acrylate copolymer (b) is one with the INCI name Acrylates Copolymer (and) Water.

12. The cosmetic composition according to one of the preceding points, wherein the anionic acrylate copolymer (a) is BALANCE® RCF (AkzoNobel) and the anionic acrylate copolymer (b) is AquaStyle® SH-100 (Ashland Inc.).

13. The cosmetic composition according to one of the preceding points which, relative to the total weight of the cosmetic composition, contains:

from about 0.1 to about 5.0% by wt of the anionic acrylate copolymer (a) and from about 0.1 to about 5.0% by wt of the anionic acrylate copolymer (b).

14. The cosmetic composition according to one of the preceding points containing, relative to the total weight of the cosmetic composition:
from about 1.5 to about 3.0% by wt of the anionic acrylate copolymer (a) and
from about 1.5 to about 3.0% by wt of the anionic acrylate copolymer (b).

15. The cosmetic composition according to one of the preceding points, wherein the composition furthermore contains at least one polymer (c) which differs from the acrylate copolymers (a) and (b), in particular an anionic or non-ionic polymer (c).

16. The cosmetic composition according to one of the preceding points, exemplified in that, relative to its total weight, it furthermore contains
c) from about 1.0 to about 10% by wt polyvinylpyrrolidone and/or vinylpyrrolidone/vinyl acetate copolymer, preferably polyvinylpyrrolidone.

17. The cosmetic composition according to point 16, exemplified in that the weight proportion of the polyvinylpyrrolidone and/or vinylpyrrolidone/vinyl acetate copolymer c) of the total weight of the cosmetic composition is from about 2.0 to about 8.5% by wt, preferably from about 3.0 to about 7.0% by wt.

18. The cosmetic composition according to one of the preceding points, wherein the composition contains water in a proportion of from about 50 to about 95% by wt, preferably between about 60 and about 90% by wt and, in particular, between about 65 and about 85% by wt, relative to the total weight of the cosmetic composition.

19. The cosmetic composition according to one of the preceding points, wherein the composition exists as a hair gel, hairspray, hair mousse or hair wax, in particular as a hair gel.

20. Use of a cosmetic composition according to one of points 1 to 19 for the temporary reshaping of keratinous fibres.

21. The use of a cosmetic composition according to one of points 1 to 19 for improving the moisture resistance of temporarily reshaped keratinous fibres.

22. A method for the temporary reshaping of keratinous fibres, in particular human hair, in which the cosmetic composition according to one of points 1 to 19 is applied to keratinous fibres.

It was surprisingly found within the framework of the present disclosure that through the combination of two constituents known per se which are used in styling products, an improved moisture resistance of styling products can be obtained. Other customarily required properties of styling products, such as high-humidity curl retention, stiffness and low tack, are retained in this case. A good combination of properties of this kind could not be expected, even when the individual components are known, and was surprising. It proved experimental that through the combination of the two components, a highly over-additive, in other words synergistic, effect in terms of moisture resistance was achieved, which manifested itself in the HHRC (High Humidity Curl Retention) test.

The term "keratinous fibres" as contemplated herein comprises skins animal pelts, wool and feathers, but particularly human hair.

The substantial constituents of the cosmetic composition as contemplated herein are the crosslinked acrylate copolymer (a) and the anionic acrylate copolymer (b) which differs from the acrylate copolymer (a).

The crosslinked anionic acrylate copolymer (a) is constructed from at least the following structural units (a1) and (a2):

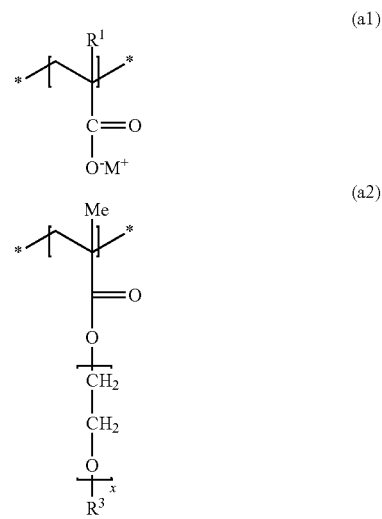

where
$R^1$ stands for a hydrogen atom or a methyl group,
$R^3$ stands for a $(C_8\text{-}C_{30})$ alkyl group,
$M^+$ stands for a physiologically compatible cation and
x stands for a whole number from 5 to 35.

The crosslinked acrylate copolymer (a) is amphiphilic due to the structural units contained. By "amphiphilic", the person skilled in the art generally understands a situation in which one and the same molecule comprises hydrophilic structural elements (for example, those with the formula (a1)) and lipophilic structural elements (for example, those with the formula (a2)).

In the above formulae and all the following formulae, there is a chemical bond identified by the symbol * for free valence of the corresponding structural fragment. In particular, metal cations of the physiologically compatible metals from the groups Ia, Ib, IIa, IIb, IIIb, VIa or VIII of the periodic system of elements, ammonium ions and also cationic organic compounds with a quaternized nitrogen atom are suitable as physiologically compatible cations M+ for compensation of the negative charge of the amphiphilic, anionic polymers. The latter are formed, for example, by the protonation of primary, secondary or tertiary organic amines with an acid or by permanent quaternization of the aforementioned organic amines. Examples of these cationic organic ammonium compounds are 2-ammonioethanol and 2-trimethylammonioethanol.

Within the meaning as contemplated herein, "crosslinked" or "crosslinking" should be understood to mean the linkage of polymer chains to one another by covalent chemical bonding, thereby forming a network. This covalent linkage of polymer chains may take place by employing direct covalent bonding or by a molecular fragment bridging the polymer chains. The molecular fragment bonds with the polymer chains bridged by the molecular fragment by employing a covalent chemical bond in each case.

The crosslinking of the crosslinked, amphiphilic, anionic polymers (a) can be preferably accomplished by using at least one crosslinking monomer. In this case, it is in turn preferable for the crosslinking monomers to be chosen from at least one compound of the group comprising polyunsaturated aromatic monomers (such as divinylbenzene, divinylnaphthalene, trivinylbenzene, for example), polyunsaturated alicyclic monomers (such as, for example, 1,2,4-trivinylcyclohexane), di-functional esters of phthalic acid (such as diallyl phthalate, for example), polyunsaturated aliphatic monomers (such as dienes, trienes, tetraenes such as isoprene, 1,3-butadiene, 1,5-hexadiene, 1,5,9-decatriene, 1,9-decadiene, 1,5-heptadiene), polyalkeneylether (such as triallyl pentaerythritol, diallyl pentaerythritol, diallyl sucrose, octaallyl sucrose, trimethylolpropane diallyl ether), polyunsaturated esters of polyalcohols or polyacids (such as 1,6-hexanediol di(meth)acrylate, tetramethylene tri(meth)acrylate, allyl acrylate, diallyl itaconate, diallyl fumarate, diallyl maleate, trimethylolpropane tri(meth)acrylate, trimethylolpropane di(meth)acrylate, polyethylene glycol di(meth) acrylate), alkylene bisacrylamides (such as methylene bisacrylamide, propylene bisacrylamide, for example) hydroxy and carboxy derivatives of the methylene bisacrylamide (such as N,N'-bismethylol methylenebisacrylamide), polyethylene glycol di(meth)acrylates (such as, for example, ethylene glycol di(meth)acrylate, diethylene glycol di(meth) acrylate, triethylene glycol di(meth)acrylate), polyunsaturated silanes (such as dimethyldivinylsilane, methyltrivinylsilane, allyldimethylvinylsilane, diallyldimethyl silane, tetravinylsilane), N-methylolacrylamide; N-alkoxy(meth) acrylamide, wherein the alkoxy group is a (C1 to C18) alkoxy group, unsaturated hydrolysable silanes (such as, for example, triethoxyvinylsilane, trisisopropoxyvinylsilane, 3-triethoxysilylpropyl-methacrylate), hydrolysable silanes (such as, for example, ethyltriethoxysilane, ethyltrimethoxysilane), epoxy-substituted hydrolysable silanes (such as, for example, 2-(3,4-epoxycyclohexyl)ethyltriethoxysilane, 3-glycidoxypropyltrimethyoxysilane), polyisocyanates (such as, for example, 1,4-diisocyanatobutane, 1,6-diisocyanatohexane, 1,4-phenylenediisocyanate, 4,4'-oxybis(phenylisocyanate), unsaturated epoxides (such as, for example, glycidylmethacrylates, allyl glycidyl ether), polyepoxides (such as diglycidyl ether, 1,2,5,6 diepoxyhexane, ethylene glycoldiglycidyl ether, for example), ethoxylated polyols (such as diols, triols and diphenols, for example, ethoxylated with 2 to 100 mol ethylene oxide per mol hydroxyl groups in each case and terminated with a polymerizable unsaturated group, such as vinyl ether, allyl ether, acrylate ester, methacrylate ester, for example; examples comprise bisphenol A ethoxylated di(meth)acrylate, bisphenol F ethoxylated di(meth)acrylate, ethoxylated trimethylolpropane tri(meth) acrylates, acrylate and methacrylate esters of polyols with at least two acrylate ester or methacrylate ester functionalities (such as, for example, trimethylolpropane triacrylate (TMPTA), trimethylolpropane ethoxylate (15) triacrylate (TMPEO15TA), trimethylolpropane dimethacrylate, triethyleneglycol dimethacrylate (TEGDMA), with 30 mol ethylene oxide ethoxylated bisphenol A-dimethacrylate (EOBDMA)).

The copolymer (a) as contemplated herein may be constructed from further structural units. In a preferred embodiment, the copolymer (a) comprises at least 30% by wt, preferably up to from about 40 to about 98% by wt and, in particular, at least about 50 to about 95% by wt, monomers (a1) and (a2). According to a preferred embodiment as contemplated herein, the copolymer (a) is, however, only composed of the units (a1) and (a2) and crosslinking units, i.e. it is made up of these structural units.

The at least one unit (a1) is a (meth)acrylic acid unit and may be a methacrylic acid and/or acrylic acid unit as contemplated herein.

x in the unit (a2) of the crosslinked acrylate copolymer (a) preferably stands for a whole number from 10 to 24, further preferably from 16 to 22, most preferably 20.

In the unit (a2) of the crosslinked acrylate copolymer (a) $R^3$ preferably stands for a ($C_{12}$-$C_{20}$) alkyl group, more preferably a ($C_{14}$-$C_{20}$) alkyl group, likewise preferably a ($C_{16}$-$C_{18}$) alkyl group. The alkyl group in this case is preferably linear, although it may also be branched. $R^3$ is more preferably a combination of linear $C_{16}$ and $C_{18}$ alkyl groups, so stearyl and cetyl groups (INCI: ceteareth).

The most preferable thing is that as the crosslinked acrylate copolymer (a), a polymer of this kind with the INCI name Acrylates/Ceteareth-20 Methacrylate Crosspolymer. Quite particularly preferably, the crosslinked acrylate copolymer (a) is one available by the commercial name BALANCE® RCF (AkzoNobel). In the latter case, this is a roughly 30% by wt dispersion in water.

Further preferred crosslinked acrylate polymers (a) bear the INCI name Acrylates/Steareth-20 Methacrylate Crosspolymer. In this case, the at least one unit (a1) is a (meth)acrylic acid unit and may be a methacrylic acid and/or acrylic acid unit, as contemplated herein. They have 20 units of ethylene oxide and are etherified with stearyl alcohol. A polymer of this kind is, for example, available by the commercial name Aculyn® 88 (Rohm & Haas). This has a solid content of roughly from about 28 to about 33% by wt and a pH value of from about 3.3 to about 4.3 in the commercially available form.

The cosmetic compositions as contemplated herein contain an anionic acrylate copolymer (b) as the second substantial constituent.

The ionic acrylate copolymer (b) is at least made up of the following monomer units: at least one (meth)acrylic acid unit (b1), at least one (meth)acrylic acid ethyl ester unit (b2) and at least one (meth)acrylic acid ester unit (b3) which differs from the (meth)acrylic acid ethyl ester unit (b2) and exhibits a hydrophobic group as the ester group.

The copolymer (b) as contemplated herein may be constructed from further monomer units. According to a preferred embodiment as contemplated herein, the copolymer (b) is, however, only made up of the units (b1), (b2) and (b3), i.e. it is made up of units derived from these monomer units.

The at least one (meth)acrylic acid unit (b1) may be a methacrylic acid or acrylic acid unit, wherein a methacrylic acid unit is preferred.

The at least one (meth)acrylic acid ethyl ester unit (b2) may be a methacrylic acid ethyl ester unit or an acrylic acid ethyl ester unit, wherein an acrylic acid ethyl ester unit is preferred.

The at least one (meth)acrylic acid ester unit (b3) may be a (meth)acrylic acid alkyl ester unit as contemplated herein. The alkyl group of the (meth)acrylic acid alkyl ester unit is used to control the hydrophobicity of the copolymer. The alkyl group is preferably a linear or branched alkyl group with from 2 to 30 carbon atoms, preferably from 3 to 12 carbon atoms. The hydrophobic group as contemplated herein may also be a hydrophobic group other than an alkyl group, e.g. an aromatic hydrocarbon ester group. An example is a substituted or unsubstituted phenyl ester group or substituted or unsubstituted alkylene phenyl ester group, e.g. a benzyl ester group.

The viscosity of the anionic acrylate copolymer (b) used in the cosmetic composition with a solid content of about 2% by wt and neutralized solution at 25° C. is preferably no more than about 60000 to about 120000 cPS.

Suitable anionic acrylate copolymers (b) are commercially available by the INCI name Acrylates Copolymer (and) Water. The most preferable is the anionic acrylate copolymer (b) AquaStyle® SH-100 Polymer from Ashland, Inc. In the commercially available form, this has a solid content of about 28 to about 32% by wt and a pH value of from about 2.1 to about 4.0.

The cosmetic composition of the present disclosure contains the acrylate copolymer (a) and acrylate copolymer (b) in customary and suitable quantities for styling agents which can be adapted for special use and manufacture.

The composition as contemplated herein may contain the crosslinked acrylate copolymer (a), for example in a quantity of from about 0.1 to about 5.0% by wt relative to the total weight of the composition as contemplated herein. Proportions of the copolymer (a) from about 1.0 to about 4.0% by wt and, in particular, from about 1.5 to about 3.0% by wt are preferred, specified in each case as the solid content of active substance in the cosmetic composition.

The cosmetic composition as contemplated herein contains the acrylate copolymer (b) relative to the total weight of the cosmetic composition, e.g. in a quantity of from about 0.1 to about 5.0% by wt, preferably from about 1.0 to about 4.0% by wt, further preferably from about 1.5 to about 3.0% by wt, specified in each case as the solid content of active substance in the cosmetic composition.

The cosmetic compositions as contemplated herein are also exemplified in particular by an improved high-humidity curl retention compared with alternative cosmetic agents, in addition to the aforementioned advantages. A weight ratio of polymers a) and b) in the cosmetic agent of from about 5:1 to about 1:5, preferably from about 3:1 to about 1:3 and, in particular, from about 2:1 to about 1:2, has proved particularly advantageous for cosmetic properties of the agent as contemplated herein.

In a particularly referred embodiment of the present disclosure, the cosmetic composition contains as the crosslinked, anionic acrylate copolymer (a) the copolymer commercially available by the name BALANCE® RCF and as the anionic acrylate copolymer (b) the copolymer commercially available by the name AquaStyle® SH-100. With this combination, particularly good results were obtained in respect of a combination of stiffness and high-humidity curl retention. This polymer combination is particularly advantageous in gel-type styling products.

Further generally required properties of styling products such as, for example, moisture resistance and low tack are likewise particularly achieved with this combination, particularly when manufactured as hair gel.

The acrylate copolymers (a) and (b) are preferably used in partially neutralized or neutralized form in the cosmetic composition. For neutralization purposes, at least one alkanolamine is preferably used. The alkanolamines that can be used as alkalization as contemplated herein are preferably chosen from primary amines with a $C_2$-$C_6$ alkyl carrier which supports at least one hydroxyl group. Particularly preferred alkanolamines are chosen from the group formed from 2-aminoethan-1-ol (monoethanolamine), tris(2-hydroxyethyl)-amine (triethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropan-1,2-diol, 2-amino-2-methyl-propan-1,3-diol. As contemplated herein, quite particularly preferred alkanolamines are chosen from the group 2-aminoethan-1-ol, 2-amino-2-methylpropan-1-ol and 2-amino-2-methyl-propan-1,3-diol. 2-amino-2-methylpropanol has proved a particularly suitable neutralization agent in this case. As contemplated herein, preferred cosmetic agents therefore contain 2-amino-2-methylpropanol. The 2-amino-2-methylpropanol is used in the agents as contemplated herein, preferably in a quantity that does not exceed the amount required for neutralization of the acrylate copolymers (a) and (b). The quantities of 2-amino-2-methylpropanol used in the compositions as contemplated herein preferably amounts to from about 80 to about 100%, particularly preferably from about 90 to about 100% and, in particular, from about 95 to about 100% of the amount required for complete neutralization of the acrylate copolymers (a) and (b). In a preferred embodiment, the weight proportion of the 2-amino-2-methylpropanol of the total weight of the cosmetic agent is from about 0.05 to about 7.0% by wt, preferably from about 0.1 to about 5.0% by wt and, in particular, from about 0.1 to about 3.0% by wt.

In summary, a preferred cosmetic composition for the temporary reshaping of keratinous fibres in respect of their total weight is:

(a) from about 0.1 to about 5.0 of at least one crosslinked acrylate copolymer which is at least constructed from the following structural units (a1) and (a2):

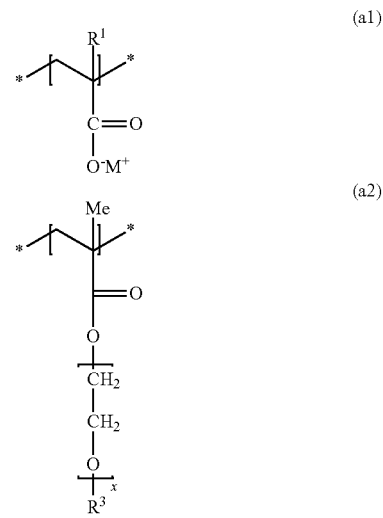

where
$R^1$ stands for a hydrogen atom or a methyl group,
$R^3$ stands for a ($C_8$-$C_{30}$) alkyl group,
$M^+$ stands for a physiologically compatible cation and
x stands for a whole number from 5 to 35
and
(b) from about 0.1 to about 5.0 of at least one anionic acrylate copolymer (b) which is constructed from at least the following monomer units:
(b1) at least one methacrylic acid unit
(b2) at least one acrylic acid ethyl ester unit
(b3) at least one methacrylic acid ester unit which is different from the acrylic acid ethyl ester unit (b2) and exhibits a hydrophobic group as the ester group.

The cosmetic composition of the present disclosure preferably contains one or more other component(s) acting as thickening agents or gelling agents which is/are different from the acrylate copolymer (a) and (b) and likewise support the film former. Examples are cationic, anionic, non-ionic or amphoteric polymers. The weight proportion of these further components of the total weight of the cosmetic composition may be comparatively low due to the presence of components (a) and (b) and is, for example, from about 0.02 to about 3% by wt, preferably from about 0.05 to about 1.5% by wt and still more preferably from about 0.2 to about 0.8% by wt.

Examples are Acrylamide/Ammonium Acrylate Copolymer, Acrylamides/DMAPA Acrylates/Methoxy PEG Methacrylate Copolymer, Acrylamidopropyltrimonium Chloride/Acrylamide Copolymer, Acrylamidopropyltrimonium Chloride/Acrylates Copolymer, Acrylates/Acetoacetoxyethyl Methacrylate Copolymer, Acrylates/Acrylamide Copolymer, Acrylates/Ammonium Methacrylate Copolymer, Acrylates/t-Butylacrylamide Copolymer, Acrylates/C1-2 Succinates/Hydroxyacrylates Copolymer, Acrylates/Lauryl Acrylate/Stearyl Acrylate/Ethylamine Oxide Methacrylate Copolymer, Acrylates/Octylacrylamide Copolymer, Acrylates/Octylacrylamide/Diphenyl Amodimethicone Copolymer, Acrylates/Stearyl Acrylate/Ethylamine Oxide Methacrylate Copolymer, Acrylates/VA Copolymer, Acrylates/VP Copolymer, Adipic Acid/Diethylenetriamine Copolymer, Adipic Acid/Dimethylaminohydroxypropyl Diethylenetriamine Copolymer, Adipic Acid/Epoxypropyl Diethylenetriamine Copolymer, Adipic Acid/Isophthalic Acid/Neopentyl Glycol/Trimethylolpropane Copolymer, Allyl Stearate/VA Copolymer, Aminoethylacrylate Phosphate/Acrylates Copolymer, Aminoethylpropanediol-Acrylates/Acrylamide Copolymer, Aminoethylpropanediol-AMPD-Acrylates/Diacetoneacrylamide Copolymer, AMP-Acrylates/Allyl Methacrylate Copolymer, AMP-Acrylates/C1-18 Alkyl Acrylates/C1-8 Alkyl Acrylamide Copolymer, AMP-Acrylates/Diacetoneacrylamide Copolymer, AMP-Acrylates/Dimethylaminoethylmethacrylate Copolymer, *Bacillus*/Rice Bran Extract/Soybean Extract Ferment Filtrate, Bis-Butyleoxyamodimethicone/PEG-60 Copolymer, Butyl Acrylate/Ethylhexyl Methacrylate Copolymer, Butyl Acrylate/Hydroxypropyl Dimethicone Acrylate Copolymer, Butylated PVP, Butyl Ester of Ethylene/MA Copolymer, Butyl Ester of PVM/MA Copolymer, Calcium/Sodium PVM/MA Copolymer, Corn Starch/Acrylamide/Sodium Acrylate Copolymer, Diethylene Glycolamine/Epichlorohydrin/Piperazine Copolymer, Dimethicone Crosspolymer, Diphenyl Amodimethicone, Ethyl Ester of PVM/MA Copolymer, Hydrolyzed Wheat Protein/PVP Crosspolymer, Isobutylene/Ethylmaleimide/Hydroxyethylmaleimide Copolymer, Isobutylene/MA Copolymer, Isobutylmethacrylate/Bis-Hydroxypropyl Dimethicone Acrylate Copolymer, Isopropyl Ester of PVM/MA Copolymer, Lauryl Acrylate Crosspolymer, Lauryl Methacrylate/Glycol Dimethacrylate Crosspolymer, MEA-Sulfite, Methacrylic Acid/Sodium Acrylamidomethyl Propane Sulfonate Copolymer, Methacryloyl Ethyl Betaine/Acrylates Copolymer, Octylacrylamide/Acrylates/Butylaminoethyl Methacrylate Copolymer, PEG/PPG-25/25 Dimethicone/Acrylates Copolymer, PEG-8/SMDI Copolymer, Polyacrylamide, Polyacrylate-6, Poly-beta-Alanine/Glutaric Acid Crosspolymer, Polybutylene Terephthalate, Polyester-1, Polyethylacrylate, Polyethylene Terephthalate, Polymethacryloyl Ethyl Betaine, Polypentaerythrityl Terephthalate, Polyperfluoroperhydrophenanthrene, Polyquaternium-1, Polyquaternium-2, Polyquaternium-4, Polyquaternium-5, Polyquaternium-6, Polyquaternium-7, Polyquaternium-8, Polyquaternium-9, Polyquaternium-10, Polyquaternium-11, Polyquaternium-12, Polyquaternium-13, Polyquaternium-14, Polyquaternium-15, Polyquaternium-16, Polyquaternium-17, Polyquaternium-18, Polyquaternium-19, Polyquaternium-20, Polyquaternium-22, Polyquaternium-24, Polyquaternium-27, Polyquaternium-28, Polyquaternium-29, Polyquaternium-30, Polyquaternium-31, Polyquaternium-32, Polyquaternium-33, Polyquaternium-34, Polyquaternium-35, Polyquaternium-36, Polyquaternium-37, Polyquaternium-39, Polyquaternium-45, Polyquaternium-46, Polyquaternium-47, Polyquaternium-48, Polyquaternium-49, Polyquaternium-50, Polyquaternium-55, Polyquaternium-56, Polysilicone-9, Polyurethane-1, Polyurethane-6, Polyurethane-10, Polyvinyl Acetate, Polyvinyl Butyral, Polyvinylcaprolactam, Polyvinylformamide, Polyvinyl Imidazolinium Acetate, Polyvinyl Methyl Ether, Potassium Butyl Ester of PVM/MA Copolymer, Potassium Ethyl Ester of PVM/MA Copolymer, PPG-70 Polyglyceryl-10 Ether, PPG-12/SMDI Copolymer, PPG-51/SMDI Copolymer, PPG-10 Sorbitol, PVM/MA Copolymer, PVP, PVP/VA/Itaconic Acid Copolymer, PVP/VA/Vinyl Propionate Copolymer, Rhizobian Gum, Rosin Acrylate, Shellac, Sodium Butyl Ester of PVM/MA Copolymer, Sodium Ethyl Ester of PVM/MA Copolymer, Sodium Polyacrylate, Sterculia Urens Gum, Terephthalic Acid/Isophthalic Acid/Sodium Isophthalic Acid Sulfonate/Glycol Copolymer, Trimethylolpropane Triacrylate, Trimethylsiloxysilylcarbamoyl Pullulan, VA/Crotonates Copolymer, VA/Crotonates/Methacryloxybenzophenone-1 Copolymer, VA/Crotonates/Vinyl Neodecanoate Copolymer, VA/Crotonates/Vinyl Propionate Copolymer, VA/DBM Copolymer, VA/Vinyl Butyl Benzoate/Crotonates Copolymer, Vinylamine/Vinyl Alcohol Copolymer, Vinyl Caprolactam/VP/Dimethylaminoethyl Methacrylate Copolymer, VP/Acrylates/Lauryl Methacrylate Copolymer, VP/Dimethylaminoethylmethacrylate Copolymer, VP/DMAPA Acrylates Copolymer, VP/Hexadecene Copolymer, VP/VA Copolymer, VP/Vinyl Caprolactam/DMAPA Acrylates Copolymer, Yeast Palmitate and Styrene/VP Copolymer.

Examples of non-ionic polymers are:

vinylpyrrolidone/vinyl ester copolymers, such as those marked under the brand Luviskol (BASF), for example. Luviskol VA 64 and Luviskol VA 73, vinylpyrrolidone/vinyl acetate copolymers in each case, are preferred non-ionic polymers.

cellulose ethers, such as hydroxypropyl cellulose, hydroxyethyl cellulose and methyl hydroxypropyl cellulose, such as those marked under the brand Culminalund Benecel (AQUALON), for example, shellac polyvinylpyrrolidone, as marked under the brand Luviskol (BASF), for example.

siloxanes. These siloxanes may be both water-soluble and also water-insoluble. Both volatile and also non-volatile siloxanes are suitable, wherein non-volatile siloxanes are understood to be those compounds with a boiling point at normal pressure above 200° C. Preferred siloxanes are polydialkylsiloxanes, such as polydimethylsiloxane, for example, polyalkylarylsiloxanes, such as polyphenylmethylsiloxane, ethoxylated polydialkylsiloxanes and also polydialkylsiloxanes which contain amine and/or hydroxy groups.

glycosidically substituted silicones.

The other component acting as a gelling agent is preferably a homopolyacrylic acid (INCI: Carbomer) which is available commercially by the name Carbopol® in different forms. The carbomer is preferably contained in a proportion of from about 0.02 to about 3% by wt, preferably from about 0.05 to about 1.5% by wt and further preferably from about 0.2 to about 0.8% by wt relative to the total weight of the cosmetic composition.

Due to its cosmetic action combined with the copolymers a) and b) as contemplated herein, preferably used film-forming polymers are, in particular, polyvinylpyrrolidones (INCI name: PVP) and also the vinylpyrrolidone/vinyl acetate copolymers (INCI name VP/VA copolymer), wherein the weight proportion of these polymers is preferably limited to quantities of between about 1.0 and about 10% by wt. Particularly preferred cosmetic compositions as contemplated herein are therefore exemplified in that they furthermore contain from about 1.0 to about 10% by wt polyvinylpyrrolidone and/or vinylpyrrolidone/vinyl acetate copolymer, preferably polyvinylpyrrolidone. Particularly preferred cosmetic agents have a weight proportion of the polyvinylpyrrolidone and/or vinylpyrrolidone/vinyl acetate copolymer c) of the total weight of the cosmetic agent of from about 2.0 to about 8.5% by wt, preferably of from about 3.0 to about 7.0% by wt.

The cosmetic composition as contemplated herein may contain further customary substances of styling products. Additional conditioning agents, in particular, should be mentioned as further suitable auxiliary and additional substances.

As a conditioning agent, the agent may, for example, contain at least one protein hydrolysate and/or one of its derivatives. Protein hydrolysates are mixed products which are obtained by the acid, alkaline or enzymatic catalysed breakdown of proteins. The term protein hydrolysates as contemplated herein also refers to total hydrolysates and also individual amino acids and derivatives thereof and mixtures of different amino acids. The molecular weight of the protein hydrolysates that can be used as contemplated herein lies between about 75, the molecular weight of glycine, and about 200,000, the molecular weight is preferably from about 75 to about 50,000 and particularly preferably from about 75 to about 20,000 Dalton.

As a conditioning agent, the agent as contemplated herein may furthermore contain at least one vitamin, a pro-vitamin, a vitamin precursor and/or a derivative thereof. In this case, preferable vitamins, pro-vitamins and vitamin precursors as contemplated herein are those which are customarily assigned to the groups A, B, C, E, F and H.

As with the addition of glycerine and/or propylene glycol, the addition of panthenol also increases the flexibility of the polymer film formed when using the agent as contemplated herein.

The agents as contemplated herein may furthermore contain at least one plant extract as the conditioning agent, but also mono- or oligosaccharides and/or lipids.

Furthermore, oil bodies are suitable as a conditioning agent. The natural and synthetic cosmetic oil bodies include, for example, vegetable oils, liquid paraffin oils, iso-paraffin oils and synthetic hydrocarbons and also Di-n-alkyl ether with a total of between 12 and 36 C atoms, in particular 12 to 24 C atoms. Preferred cosmetic agents as contemplated herein contain at last one oil body, preferably at least one oil body from the group of silicon oils. The group of silicon oils includes, in particular, the dimethicones, which also include the cyclomethicones, the amino-functional silicones and also the dimethiconols. The dimethicones may be both linear and also branched and also cyclical or cyclical and branched. Suitable silicon oils or silicon gums are, in particular, dialkyl- and alkylarylsiloxanes, such as, for example, dimethylpolysiloxane and methylphenylpolysiloxane, as well as alkolyzed, quaternized or also anionic derivatives thereof. Cyclical and linear polydialkylsiloxanes, alkoxylized and/or aminized derivatives thereof, dihydroxypolydimethylsiloxanes and polyphenylalkylsiloxanes are preferred.

Ester oils, in other words, esters of 6-C30-fatty acids with C2-C30-fatty alcohols, preferably mono-esters of the fatty acids with alcohols with 2 to 24 C-atoms such as, for example, isopropyl myristate (Rilanit® IPM), isononanoic acid-C16-18-alkyl ester (Cetiol® SN), 2-ethylhexyl palmitate (Cegesoft® 24), stearic acid-2-ethylhexyl ester (Cetiol® 868), cetyloleate, glycerol tricaprylate, coconut oil alcohol-caprinate/-caprylate (Cetiol® LC), n-butylstearate, oleyl erucate (Cetiol® J 600), isopropyl palmitate (Rilanit® IPP), oleyl oleate (Cetiol®), lauric acid hexylester (Cetiol® A), di-n-butyladipate (Cetiol® B), myristyl myristat (Cetiol® MM), cetearyl isononanoate (Cetiol® SN), oleic acid decyl ester (Cetiol® V) are further preferred conditioning oil bodies.

Furthermore, dicarbonic acid esters, symmetrical, asymmetrical or cyclical esters of carbonic acid with fatty alcohols, tri-fatty acid esters of saturated and/or unsaturated linear and/or branched fatty acids with glycerine or fatty acid partial glycerides, taken to include monoglycerides, diglycerides and technical mixtures thereof, are suitable as conditioning agents.

Furthermore, emulsifiers or surface-active agents are preferably contained in the composition as contemplated herein. PEG derivatives of hydrated ricinoleic acid which are available by the name PEG Hydrogenated Castor Oil, PEG-36 Hydrogenated Castor Oil or PEG-40 Hydrogenated Castor Oil, PEG-36 Hydrogenated Castor Oil or PEG-40 Hydrogenated Castor Oil, for example, are preferred. The use of PEG-40 Hydrogenated Castor Oil is preferred as contemplated herein. These are preferably contained in a quantity of from about 0.05 to about 1.5% by wt, more preferably from about 0.1 to about 1.0% by wt, likewise preferably from about 0.2 to about 0.8% by wt or from about 0.3 to about 0.6% by wt.

The cosmetic agents as contemplated herein contain the ingredients or active agents in a cosmetically acceptable substrate.

Preferred cosmetically acceptable substrates are aqueous, alcoholic or aqueous-alcoholic media having, for example, about 10% by wt water calculated based on the total weight of the agent.

Particularly preferably, the cosmetic substrate as contemplated herein contains water, particularly in the quantity that the cosmetic agent, calculated based on the total weight of the agent, contains at least about 10% by wt, in particular at least about 20.0% by wt, most preferably at least about 40% by wt water. Quite particularly preferred cosmetic agents exhibit a water proportion of between about 50 and about 95% by wt, preferably between about 60 and about 90% by wt and, in particular, between about 65 and about 85% by wt relative to their total weight.

The lower alcohols with 1 to 4 carbon items such as ethanol or isopropanol, for example, customarily used for cosmetic purposes may in particular be contained as alcohols.

Examples of water-soluble solvents as co-solvents are glycerine and/or ethylene glycol and/or 1,2 propylene glycol in a quantity of 0 to about 30% by wt relative to the total agent.

Tabular Overview

The composition of a few preferred cosmetic agents can be inferred from the following tables (figures in % by wt relative to the total weight of the cosmetic agent, unless otherwise specified).

|  | Formula 1 | Formula 2 | Formula 3 | Formula 4 | Formula 5 |
| --- | --- | --- | --- | --- | --- |
| Copolymer a) | 0.1 to 5.0 | 1.0 to 4.0 | 1.0 to 4.0 | 1.5 to 3.0 | 1.5 to 3.0 |
| Copolymer b) | 0.1 to 5.0 | 0.1 to 5.0 | 1.0 to 4.0 | 1.0 to 4.0 | 1.5 to 3.0 |
| Misc | add 100 | add 100 | add 100 | add 100 | add 100 |

|  | Formula 1a | Formula 2a | Formula 3a | Formula 4a | Formula 5a |
| --- | --- | --- | --- | --- | --- |
| Copolymer a): Acrylates/Ceteareth-20 Methacrylate Crosspolymer | 0.1 to 5.0 | 1.0 to 4.0 | 1.0 to 4.0 | 1.5 to 3.0 | 1.5 to 3.0 |
| Copolymer b): Acrylates Copolymer (and) Water | 0.1 to 5.0 | 0.1 to 5.0 | 1.0 to 4.0 | 1.0 to 4.0 | 1.5 to 3.0 |
| Misc | add 100 | add 100 | add 100 | add 100 | add 100 |

|  | Formula 1b | Formula 2b | Formula 3b | Formula 4b | Formula 5b |
| --- | --- | --- | --- | --- | --- |
| Copolymer a): BALANCE ® RCF (figures as solid content) | 0.1 to 5.0 | 1.0 to 4.0 | 1.0 to 4.0 | 1.5 to 3.0 | 1.5 to 3.0 |
| Copolymer b): AquaStyle ® SH-100 (figures as solid content) | 0.1 to 5.0 | 0.1 to 5.0 | 1.0 to 4.0 | 1.0 to 4.0 | 1.5 to 3.0 |
| Misc | add 100 | add 100 | add 100 | add 100 | add 100 |

|  | Formula 6 | Formula 7 | Formula 8 | Formula 9 | Formula 10 |
| --- | --- | --- | --- | --- | --- |
| Copolymer a): | 0.1 to 5.0 | 1.0 to 4.0 | 1.0 to 4.0 | 1.5 to 3.0 | 1.5 to 3.0 |
| Copolymer b): | 0.1 to 5.0 | 0.1 to 5.0 | 1.0 to 4.0 | 1.0 to 4.0 | 1.5 to 3.0 |
| Polyvinylpyrrolidone | 1.0 to 10 | 2.0 to 8.5 | 2.0 to 8.5 | 3.0 to 7.0 | 3.0 to 7.0 |
| Misc | add 100 | add 100 | add 100 | add 100 | add 100 |

|  | Formula 6a | Formula 7a | Formula 8a | Formula 9a | Formula 10a |
| --- | --- | --- | --- | --- | --- |
| Copolymer a): Acrylates/Ceteareth-20 Methacrylate Crosspolymer | 0.1 to 5.0 | 1.0 to 4.0 | 1.0 to 4.0 | 1.5 to 3.0 | 1.5 to 3.0 |
| Copolymer b): Acrylates Copolymer (and) Water | 0.1 to 5.0 | 0.1 to 5.0 | 1.0 to 4.0 | 1.0 to 4.0 | 1.5 to 3.0 |
| Polyvinylpyrrolidone | 1.0 to 10 | 2.0 to 8.5 | 2.0 to 8.5 | 3.0 to 7.0 | 3.0 to 7.0 |
| Misc | add 100 | add 100 | add 100 | add 100 | add 100 |

|  | Formula 6b | Formula 7b | Formula 8b | Formula 9b | Formula 10b |
| --- | --- | --- | --- | --- | --- |
| Copolymer a): BALANCE ® RCF (figures as solid content) | 0.1 to 5.0 | 1.0 to 4.0 | 1.0 to 4.0 | 1.5 to 3.0 | 1.5 to 3.0 |
| Copolymer b): AquaStyle ® SH-100 (figures as solid content) | 0.1 to 5.0 | 0.1 to 5.0 | 1.0 to 4.0 | 1.0 to 4.0 | 1.5 to 3.0 |
| Polyvinylpyrrolidone | 1.0 to 10 | 2.0 to 8.5 | 2.0 to 8.5 | 3.0 to 7.0 | 3.0 to 7.0 |
| Misc | add 100 | add 100 | add 100 | add 100 | add 100 |

|  | Formula 11 | Formula 12 | Formula 13 | Formula 14 | Formula 15 |
| --- | --- | --- | --- | --- | --- |
| Copolymer a): | 0.1 to 5.0 | 1.0 to 4.0 | 1.0 to 4.0 | 1.5 to 3.0 | 1.5 to 3.0 |
| Copolymer b): | 0.1 to 5.0 | 0.1 to 5.0 | 1.0 to 4.0 | 1.0 to 4.0 | 1.5 to 3.0 |
| Vinylpyrrolidone/vinyl acetate copolymer | 1.0 to 10 | 2.0 to 8.5 | 2.0 to 8.5 | 3.0 to 7.0 | 3.0 to 7.0 |
| Misc | add 100 | add 100 | add 100 | add 100 | add 100 |

|  | Formula 11a | Formula 12a | Formula 13a | Formula 14a | Formula 15a |
| --- | --- | --- | --- | --- | --- |
| Copolymer a): Acrylates/Ceteareth-20 Methacrylate Crosspolymer | 0.1 to 5.0 | 1.0 to 4.0 | 1.0 to 4.0 | 1.5 to 3.0 | 1.5 to 3.0 |

-continued

| | | | | | |
|---|---|---|---|---|---|
| Copolymer b): Acrylates Copolymer (and) Water | 0.1 to 5.0 | 0.1 to 5.0 | 1.0 to 4.0 | 1.0 to 4.0 | 1.5 to 3.0 |
| Vinylpyrrolidone/ vinyl acetate copolymer | 0.1 to 5.0 | 0.1 to 5.0 | 1.0 to 4.0 | 1.0 to 4.0 | 1.5 to 3.0 |
| Misc | add 100 | add 100 | add 100 | add 100 | add 100 |

| | Formula 11b | Formula 12b | Formula 13b | Formula 14b | Formula 15b |
|---|---|---|---|---|---|
| Copolymer a): BALANCE ® RCF (figures as solid content) | 0.1 to 5.0 | 1.0 to 4.0 | 1.0 to 4.0 | 1.5 to 3.0 | 1.5 to 3.0 |
| Copolymer b): AquaStyle ® SH-100 (figures as solid content) | 0.1 to 5.0 | 0.1 to 5.0 | 1.0 to 4.0 | 1.0 to 4.0 | 1.5 to 3.0 |
| Vinylpyrrolidone/ Vinyl Acetate Copolymer | 1.0 to 10 | 2.0 to 8.5 | 2.0 to 8.5 | 3.0 to 7.0 | 3.0 to 7.0 |
| Misc | add 100 | add 100 | add 100 | add 100 | add 100 |

| | Formula 16 | Formula 17 | Formula 18 | Formula 19 | Formula 20 |
|---|---|---|---|---|---|
| Copolymer a): | 0.1 to 5.0 | 1.0 to 4.0 | 1.0 to 4.0 | 1.5 to 3.0 | 1.5 to 3.0 |
| Copolymer b): | 0.1 to 5.0 | 0.1 to 5.0 | 1.0 to 4.0 | 1.0 to 4.0 | 1.5 to 3.0 |
| Carbomer | 0.02 to 3.0 | 0.05 to 2.0 | 0.05 to 1.5 | 0.2 to 1.0 | 0.4 to 0.8 |
| Misc | add 100 | add 100 | add 100 | add 100 | add 100 |

| | Formula 16a | Formula 17a | Formula 18a | Formula 19a | Formula 20a |
|---|---|---|---|---|---|
| Copolymer a): Acrylates/ Ceteareth-20 Methacrylate Crosspolymer | 0.1 to 5.0 | 1.0 to 4.0 | 1.0 to 4.0 | 1.5 to 3.0 | 1.5 to 3.0 |
| Copolymer b): Acrylates Copolymer (and) Water | 0.1 to 5.0 | 0.1 to 5.0 | 1.0 to 4.0 | 1.0 to 4.0 | 1.5 to 3.0 |
| Carbomer | 0.02 to 3.0 | 0.05 to 2.0 | 0.05 to 1.5 | 0.2 to 1.0 | 0.4 to 0.8 |
| Misc | add 100 | add 100 | add 100 | add 100 | add 100 |

| | Formula 16b | Formula 17b | Formula 18b | Formula 19b | Formula 20b |
|---|---|---|---|---|---|
| Copolymer a): BALANCE ® RCF (figures as solid content) | 0.1 to 5.0 | 1.0 to 4.0 | 1.0 to 4.0 | 1.5 to 3.0 | 1.5 to 3.0 |
| Copolymer b): AquaStyle ® SH-100 (figures as solid content) | 0.1 to 5.0 | 0.1 to 5.0 | 1.0 to 4.0 | 1.0 to 4.0 | 1.5 to 3.0 |
| Carbomer | 0.02 to 3.0 | 0.05 to 2.0 | 0.05 to 1.5 | 0.2 to 1.0 | 0.4 to 0.8 |
| Misc | add 100 | add 100 | add 100 | add 100 | add 100 |

| | Formula 21 | Formula 22 | Formula 23 | Formula 24 | Formula 25 |
|---|---|---|---|---|---|
| Copolymer a): | 0.1 to 5.0 | 1.0 to 4.0 | 1.0 to 4.0 | 1.5 to 3.0 | 1.5 to 3.0 |
| Copolymer b): | 0.1 to 5.0 | 0.1 to 5.0 | 1.0 to 4.0 | 1.0 to 4.0 | 1.5 to 3.0 |
| PEG-40 Hydrogenated Castor Oil | 0.05 to 1.5 | 0.1 to 1.0 | 0.2 to 0.9 | 0.3 to 0.8 | 0.4 to 0.6 |
| Misc | add 100 | add 100 | add 100 | add 100 | add 100 |

| | Formula 21a | Formula 22a | Formula 23a | Formula 24a | Formula 25a |
|---|---|---|---|---|---|
| Copolymer a): Acrylates/ Ceteareth-20 Methacrylate Crosspolymer | 0.1 to 5.0 | 1.0 to 4.0 | 1.0 to 4.0 | 1.5 to 3.0 | 1.5 to 3.0 |
| Copolymer b): Acrylates Copolymer (and) Water | 0.1 to 5.0 | 0.1 to 5.0 | 1.0 to 4.0 | 1.0 to 4.0 | 1.5 to 3.0 |

|  | | | | | |
|---|---|---|---|---|---|
| PEG-40 Hydrogenated Castor Oil | 0.05 to 1.5 | 0.1 to 1.0 | 0.2 to 0.9 | 0.3 to 0.8 | 0.4 to 0.6 |
| Misc | add 100 | add 100 | add 100 | add 100 | add 100 |
|  | Formula 21b | Formula 22b | Formula 23b | Formula 24b | Formula 25b |
| Copolymer a): BALANCE ® RCF (figures as solid content) | 0.1 to 5.0 | 1.0 to 4.0 | 1.0 to 4.0 | 1.5 to 3.0 | 1.5 to 3.0 |
| Copolymer b): AquaStyle ® SH-100 (figures as solid content) | 0.1 to 5.0 | 0.1 to 5.0 | 1.0 to 4.0 | 1.0 to 4.0 | 1.5 to 3.0 |
| PEG-40 Hydrogenated Castor Oil | 0.05 to 1.5 | 0.1 to 1.0 | 0.2 to 0.9 | 0.3 to 0.8 | 0.4 to 0.6 |
| Misc | add 100 | add 100 | add 100 | add 100 | add 100 |
|  | Formula 26 | Formula 27 | Formula 28 | Formula 29 | Formula 30 |
| Copolymer a): | 0.1 to 5.0 | 1.0 to 4.0 | 1.0 to 4.0 | 1.5 to 3.0 | 1.5 to 3.0 |
| Copolymer b): | 0.1 to 5.0 | 0.1 to 5.0 | 1.0 to 4.0 | 1.0 to 4.0 | 1.5 to 3.0 |
| Water | 50 to 95 | 50 to 95 | 60 to 90 | 60 to 90 | 65 to 85 |
| Misc | add 100 | add 100 | add 100 | add 100 | add 100 |
|  | Formula 26a | Formula 27a | Formula 28a | Formula 29a | Formula 30a |
| Copolymer a): Acrylates/ Ceteareth-20 Methacrylate Crosspolymer | 0.1 to 5.0 | 1.0 to 4.0 | 1.0 to 4.0 | 1.5 to 3.0 | 1.5 to 3.0 |
| Copolymer b): Acrylates Copolymer (and) Water | 0.1 to 5.0 | 0.1 to 5.0 | 1.0 to 4.0 | 1.0 to 4.0 | 1.5 to 3.0 |
| Water | 50 to 95 | 50 to 95 | 60 to 90 | 60 to 90 | 65 to 85 |
| Misc | add 100 | add 100 | add 100 | add 100 | add 100 |
|  | Formula 26b | Formula 27b | Formula 28b | Formula 29b | Formula 30b |
| Copolymer a): BALANCE ® RCF (figures as solid content) | 0.1 to 5.0 | 1.0 to 4.0 | 1.0 to 4.0 | 1.5 to 3.0 | 1.5 to 3.0 |
| Copolymer b): AquaStyle ® SH-100 | 0.1 to 5.0 | 0.1 to 5.0 | 1.0 to 4.0 | 1.0 to 4.0 | 1.5 to 3.0 |
| Water | 50 to 95 | 50 to 95 | 60 to 90 | 60 to 90 | 65 to 85 |
| Misc | add 100 | add 100 | add 100 | add 100 | add 100 |
|  | Formula 31 | Formula 32 | Formula 33 | Formula 34 | Formula 35 |
| Copolymer a): | 0.1 to 5.0 | 1.0 to 4.0 | 1.0 to 4.0 | 1.5 to 3.0 | 1.5 to 3.0 |
| Copolymer b): | 0.1 to 5.0 | 0.1 to 5.0 | 1.0 to 4.0 | 1.0 to 4.0 | 1.5 to 3.0 |
| Polyvinylpyrrolidone | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | add 100 | add 100 | add 100 | add 100 | add 100 |
|  | Formula 31a | Formula 32a | Formula 33a | Formula 34a | Formula 35a |
| Copolymer a): Acrylates/ Ceteareth-20 Methacrylate Crosspolymer | 0.1 to 5.0 | 1.0 to 4.0 | 1.0 to 4.0 | 1.5 to 3.0 | 1.5 to 3.0 |
| Copolymer b): Acrylates Copolymer (and) Water | 0.1 to 5.0 | 0.1 to 5.0 | 1.0 to 4.0 | 1.0 to 4.0 | 1.5 to 3.0 |
| Polyvinylpyrrolidone | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | add 100 | add 100 | add 100 | add 100 | add 100 |
|  | Formula 31b | Formula 32b | Formula 33b | Formula 34b | Formula 35b |
| Copolymer a): BALANCE ® RCF | 0.1 to 5.0 | 1.0 to 4.0 | 1.0 to 4.0 | 1.5 to 3.0 | 1.5 to 3.0 |

|  | | | | | |
|---|---|---|---|---|---|
| (figures as solid content) | | | | | |
| Copolymer b): AquaStyle ® SH-100 | 0.1 to 5.0 | 0.1 to 5.0 | 1.0 to 4.0 | 1.0 to 4.0 | 1.5 to 3.0 |
| Polyvinylpyrrolidone | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | add 100 | add 100 | add 100 | add 100 | add 100 |

|  | Formula 36 | Formula 37 | Formula 38 | Formula 39 | Formula 40 |
|---|---|---|---|---|---|
| Copolymer a): | 0.1 to 5.0 | 1.0 to 4.0 | 1.0 to 4.0 | 1.5 to 3.0 | 1.5 to 3.0 |
| Copolymer b): | 0.1 to 5.0 | 0.1 to 5.0 | 1.0 to 4.0 | 1.0 to 4.0 | 1.5 to 3.0 |
| Vinylpyrrolidone/ Vinyl Acetate Copolymer | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | add 100 | add 100 | add 100 | add 100 | add 100 |

|  | Formula 36a | Formula 37a | Formula 38a | Formula 39a | Formula 40a |
|---|---|---|---|---|---|
| Copolymer a): Acrylates/ Ceteareth-20 Methacrylate Crosspolymer | 0.1 to 5.0 | 1.0 to 4.0 | 1.0 to 4.0 | 1.5 to 3.0 | 1.5 to 3.0 |
| Copolymer b): Acrylates Copolymer (and) Water | 0.1 to 5.0 | 0.1 to 5.0 | 1.0 to 4.0 | 1.0 to 4.0 | 1.5 to 3.0 |
| Vinylpyrrolidone/ Vinyl Acetate Copolymer | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | add 100 | add 100 | add 100 | add 100 | add 100 |

|  | Formula 36b | Formula 37b | Formula 38b | Formula 39b | Formula 40b |
|---|---|---|---|---|---|
| Copolymer a): BALANCE ® RCF (figures as solid content) | 0.1 to 5.0 | 1.0 to 4.0 | 1.0 to 4.0 | 1.5 to 3.0 | 1.5 to 3.0 |
| Copolymer b): AquaStyle ® SH-100 | 0.1 to 5.0 | 0.1 to 5.0 | 1.0 to 4.0 | 1.0 to 4.0 | 1.5 to 3.0 |
| Vinyolpyrrolidone/ Vinyl Acetate Copolymer | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | add 100 | add 100 | add 100 | add 100 | add 100 |

|  | Formula 41 | Formula 42 | Formula 43 | Formula 44 | Formula 45 |
|---|---|---|---|---|---|
| Copolymer a): | 0.1 to 5.0 | 1.0 to 4.0 | 1.0 to 4.0 | 1.5 to 3.0 | 1.5 to 3.0 |
| Copolymer b): | 0.1 to 5.0 | 0.1 to 5.0 | 1.0 to 4.0 | 1.0 to 4.0 | 1.5 to 3.0 |
| Carbomer | 0.02 to 3.0 | 0.05 to 2.0 | 0.05 to 1.5 | 0.2 to 1.0 | 0.4 to 0.8 |
| Water | 50 to 95 | 50 to 95 | 60 to 90 | 60 to 90 | 65 to 85 |
| Misc | add 100 | add 100 | add 100 | add 100 | add 100 |

|  | Formula 41a | Formula 42a | Formula 43a | Formula 44a | Formula 45a |
|---|---|---|---|---|---|
| Copolymer a): Acrylates/ Ceteareth-20 Methacrylate Crosspolymer | 0.1 to 5.0 | 1.0 to 4.0 | 1.0 to 4.0 | 1.5 to 3.0 | 1.5 to 3.0 |
| Copolymer b): Acrylates Copolymer (and) Water | 0.1 to 5.0 | 0.1 to 5.0 | 1.0 to 4.0 | 1.0 to 4.0 | 1.5 to 3.0 |
| Carbomer | 0.02 to 3.0 | 0.05 to 2.0 | 0.05 to 1.5 | 0.2 to 1.0 | 0.4 to 0.8 |
| Water | 50 to 95 | 50 to 95 | 60 to 90 | 60 to 90 | 65 to 85 |
| Misc | add 100 | add 100 | add 100 | add 100 | add 100 |

|  | Formula 41b | Formula 42b | Formula 43b | Formula 44b | Formula 45b |
|---|---|---|---|---|---|
| Copolymer a): BALANCE ® RCF (figures as solid content) | 0.1 to 5.0 | 1.0 to 4.0 | 1.0 to 4.0 | 1.5 to 3.0 | 1.5 to 3.0 |

-continued

| | | | | | |
|---|---|---|---|---|---|
| Copolymer b):<br>AquaStyle ® SH-100 | 0.1 to 5.0 | 0.1 to 5.0 | 1.0 to 4.0 | 1.0 to 4.0 | 1.5 to 3.0 |
| Carbomer | 0.02 to 3.0 | 0.05 to 2.0 | 0.05 to 1.5 | 0.2 to 1.0 | 0.4 to 0.8 |
| Water | 50 to 95 | 50 to 95 | 60 to 90 | 60 to 90 | 65 to 85 |
| Misc | add 100 | add 100 | add 100 | add 100 | add 100 |
| | Formula 46 | Formula 47 | Formula 48 | Formula 49 | Formula 50 |
| Copolymer a): | 0.1 to 5.0 | 1.0 to 4.0 | 1.0 to 4.0 | 1.5 to 3.0 | 1.5 to 3.0 |
| Copolymer b): | 0.1 to 5.0 | 0.1 to 5.0 | 1.0 to 4.0 | 1.0 to 4.0 | 1.5 to 3.0 |
| PEG-40 Hydrogenated Castor Oil | 0.05 to 1.5 | 0.1 to 1.0 | 0.2 to 0.9 | 0.3 to 0.8 | 0.4 to 0.6 |
| Water | 50 to 95 | 50 to 95 | 60 to 90 | 60 to 90 | 65 to 85 |
| Misc | add 100 | add 100 | add 100 | add 100 | add 100 |
| | Formula 46a | Formula 47a | Formula 48a | Formula 49a | Formula 50a |
| Copolymer a):<br>Acrylates/Ceteareth-20 Methacrylate Crosspolymer | 0.1 to 5.0 | 1.0 to 4.0 | 1.0 to 4.0 | 1.5 to 3.0 | 1.5 to 3.0 |
| Copolymer b):<br>Acrylates Copolymer (and) Water | 0.1 to 5.0 | 0.1 to 5.0 | 1.0 to 4.0 | 1.0 to 4.0 | 1.5 to 3.0 |
| PEG-40 Hydrogenated Castor Oil | 0.05 to 1.5 | 0.1 to 1.0 | 0.2 to 0.9 | 0.3 to 0.8 | 0.4 to 0.6 |
| Water | 50 to 95 | 50 to 95 | 60 to 90 | 60 to 90 | 65 to 85 |
| Misc | add 100 | add 100 | add 100 | add 100 | add 100 |
| | Formula 46b | Formula 47b | Formula 48b | Formula 49b | Formula 50b |
| Copolymer a):<br>BALANCE ® RCF<br>(figures as solid content) | 0.1 to 5.0 | 1.0 to 4.0 | 1.0 to 4.0 | 1.5 to 3.0 | 1.5 to 3.0 |
| Copolymer b):<br>AquaStyle ® SH-100<br>(figures as solid content) | 0.1 to 5.0 | 0.1 to 5.0 | 1.0 to 4.0 | 1.0 to 4.0 | 1.5 to 3.0 |
| PEG-40 Hydrogenated Castor Oil | 0.05 to 1.5 | 0.1 to 1.0 | 0.2 to 0.9 | 0.3 to 0.8 | 0.4 to 0.6 |
| Water | 50 to 95 | 50 to 95 | 60 to 90 | 60 to 90 | 65 to 85 |
| Misc | add 100 | add 100 | add 100 | add 100 | add 100 |

"Misc" as contemplated herein denotes a cosmetic substrate, in particular (unless listed separately) water and possibly other customary constituents of styling products.

The cosmetic composition of the present disclosure may be manufactured in the customary forms for the temporary reshaping of hair, e.g. as hair gel, hair spray, hair mousse or hair wax. Manufacture as hair gel is preferable.

Both hair mousses and also hair sprays require the presence of propellants. As contemplated herein, however, no or only small amounts of hydrocarbons should be used for this purpose. Propane, propane/butane mixtures and dimethyl ether are particularly suitable propellants as contemplated herein.

The present disclosure also relates to the use of cosmetic compositions as contemplated herein for the temporary reshaping of keratinous fibres, in particular human hair, and also a method for the temporary reshaping of keratinous fibres, in particular human hair, in which the cosmetic composition as contemplated herein is applied to keratinous fibres.

A further object to this patent application is the use of a cosmetic composition as contemplated herein in order to improve the moisture resistance of temporarily reshaped keratinous fibres.

Examples

The following hair gels were produced:

| Component/raw material | INCI name or chemical name | V1 | V2 | E1 |
|---|---|---|---|---|
| BALANCE ® RCF[1] | Acrylates/Ceteareth-20 Methacrylate Crosspolymer | 16.5 | — | 8.25 |
| AquaStyle ® SH-100[2] | Acrylates Copolymer (and) Water | — | 16.5 | 8.25 |
| AMP-ULTRA PC 2000 | Aminomethyl Propanol | 1.4 | 0.3 | 0.8 |
| Water | | 82.1 | 83.2 | 82.7 |
| Total | | 100 | 100 | 100 |

[1] 30% by wt active substance in water
[2] 30% by wt active substance in water

The quantity data in the table are indicated in % by wt of the respective raw material, relative to the total composition. The polymer content in each of the compositions V1, V2 and E1 was 5.0% by wt.

For the styling agents obtained, the moisture resistance was determined (mean value when determining on 5 hair strands in each case) on clean curling hair strands by employing an HHCR test (High Humidity Curl Retention Test: 6 hrs).

|      | V1  | V2  | E1  |
| ---- | --- | --- | --- |
| HHCR | 87% | 72% | 99% |

The polymer combination E1 as contemplated herein therefore showed a clear over-additive, synergistic effect in relation to moisture resistance.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A cosmetic composition for the temporary reshaping of keratinous fibres, the cosmetic composition consisting of:
    (a) a copolymer (a) having the INCI name Acrylates/Ceteareth-20 Methacrylate Crosspolymer, wherein the copolymer (a) is present in the cosmetic composition in an amount of from about 1.5 to about 3.0 weight percent, based on a total weight of the cosmetic composition,
    (b) a copolymer (b) having the INCI name Acrylates Copolymer and Water, wherein the copolymer (b) is present in the cosmetic composition in an amount of from about 1.5 to about 3.0 weight percent, based on the total weight of the cosmetic composition;
    aminomethyl propanol; and
    water.

2. The cosmetic composition according to claim 1, wherein the copolymer (a) is present in the cosmetic composition in an amount of about 2.5 weight percent, based on the total weight of the cosmetic composition, and the copolymer (b) is present in the cosmetic composition in an amount of about 2.5 weight percent, based on the total weight of the cosmetic composition.

3. A method for the temporary reshaping of keratinous fibres, the method comprising applying the cosmetic composition according to claim 1 to keratinous fibres.

4. The cosmetic composition according to claim 1, wherein the aminomethyl propanol is present in the cosmetic composition in an amount of from about 0.1 to about 3.0 weight percent, based on the total weight of the cosmetic composition.

5. The cosmetic composition according to claim 1, wherein the copolymer (b) exhibits a viscosity of from about 60000 to about 120000 cPs where there is a solid content of about 2% by wt. in an aqueous neutralised solution at 25° C.

6. The cosmetic composition according to claim 1, wherein the aminomethyl propanol is present in the cosmetic composition in an amount of about 0.8 weight percent, based on the total weight of the cosmetic composition.

7. The cosmetic composition according to claim 1, wherein the aminomethyl propanol is 2-amino-2 methylpropanol.

8. The cosmetic composition according to claim 7, wherein the cosmetic composition, relative to the total weight of the cosmetic composition,
    comprises the 2-amino-2-methylpropanol from about 0.1 to about 3.0% by wt.

9. The cosmetic composition according to claim 1, wherein the composition comprises water in a proportion of from about 50 to about 95% by wt. relative to the total weight of the cosmetic composition.

* * * * *